US00RE47609E

(19) United States
(12) Reissued Patent
Hamadeh et al.

(10) Patent Number: US RE47,609 E
(45) Date of Reissued Patent: Sep. 17, 2019

(54) SYSTEM FOR DETECTING BONE CANCER METASTASES

(71) Applicant: Exini Diagnostics AB, Lund (SE)

(72) Inventors: Iman Hamadeh, Göteborg (SE); Pierre Nordblom, Göteborg (SE); Karl Sjöstrand, Atlantic Highlands, NJ (US)

(73) Assignee: Exini Diagnostics AB, Lund (SE)

(21) Appl. No.: 15/282,422

(22) Filed: Sep. 30, 2016

Related U.S. Patent Documents

Reissue of:
(64) Patent No.: 8,855,387
Issued: Oct. 7, 2014
Appl. No.: 13/639,747
PCT Filed: Dec. 23, 2008
PCT No.: PCT/SE2008/000746
§ 371 (c)(1),
(2) Date: Jan. 2, 2013
PCT Pub. No.: WO2009/084995
PCT Pub. Date: Jul. 9, 2009

U.S. Applications:
(60) Provisional application No. 61/017,192, filed on Dec. 28, 2007.

(51) Int. Cl.
*G06T 7/00* (2017.01)
*G06K 9/00* (2006.01)

(52) U.S. Cl.
CPC ..... *G06T 7/0012* (2013.01)

(58) Field of Classification Search
CPC ..... G06T 7/0012
USPC ..... 382/128
See application file for complete search history.

(56) References Cited

U.S. PATENT DOCUMENTS 7,450,747 B2 * 11/2008 Jabri ..... G16H 40/63 382/132
7,970,194 B2 * 6/2011 Kimura ..... G01R 33/56341 324/309
8,211,401 B2 7/2012 Babich et al.
8,538,166 B2 * 9/2013 Gordon et al. ..... 382/201
8,705,887 B2 * 4/2014 Ma et al. ..... 382/275
8,778,305 B2 7/2014 Pomper et al.
8,855,387 B2 10/2014 Hamadeh et al.
8,962,799 B2 2/2015 Babich et al.
(Continued)

FOREIGN PATENT DOCUMENTS

EP 1426903 A2 6/2004
EP 1508872 A1 2/2005
(Continued)

OTHER PUBLICATIONS

Guimond, A. et al., Average Brain Models: A Convergence Study, Computer Vision and Image Understanding, 77:192-210 (2000).
(Continued)

*Primary Examiner* — Joseph R Pokrzywa
(74) *Attorney, Agent, or Firm* — Choate, Hall & Stewart LLP; William R. Haulbrook; Ronen Adato

(57) ABSTRACT

The invention relates to a detection system for automatic detection of bone cancer metastases from a set of isotope bone scan images of a patients skeleton, the system comprising a shape identifier unit, a hotspot detection unit, a hotspot feature extraction unit, a first artificial neural network unit, a patient feature extraction unit, and a second artificial neural network unit.

22 Claims, 6 Drawing Sheets

(56) References Cited

U.S. PATENT DOCUMENTS

| | | | | |
|---|---|---|---|---|
| 2003/0215120 | A1* | 11/2003 | Uppaluri | A61B 6/482 382/128 |
| 2006/0062425 | A1 | 3/2006 | Shen et al. | |
| 2007/0081712 | A1 | 4/2007 | Huang | |
| 2007/0081713 | A1* | 4/2007 | Jerebko | G06T 7/0012 382/128 |
| 2007/0100225 | A1* | 5/2007 | Maschke | A61B 6/032 600/407 |
| 2015/0110716 | A1 | 4/2015 | Armor | |
| 2016/0203263 | A1 | 7/2016 | Maier et al. | |
| 2018/0144828 | A1 | 5/2018 | Baker | |

FOREIGN PATENT DOCUMENTS

| | | | |
|---|---|---|---|
| WO | WO-9905503 | A2 | 2/1999 |
| WO | WO-2007062135 | A2 | 5/2007 |
| WO | WO-2009084995 | A1 | 7/2009 |
| WO | WO-2018/081354 | A1 | 5/2018 |

OTHER PUBLICATIONS

Hajnal, J. et al., 4.4 Intensity, Size, and Skew Correction; 7.1 Introduction; 7.2 Methods; 7.3 Image Interpretation—General, In: Medical Image Registration, CRC Press LLC, 80-81:144-148 (2001).

Huang, J.-H. et al., A Set of Image Processing Algorithms for Computer-Aided Diagnosis in Nuclear Medicine Whole Body Bone Scan Images, IEEE Transactions on Nuclear Science, 54(3):514-522 (2007).

International Preliminary Report on Patentability, International Application Serial No. PCT/SE2008/000746, 12 pages, dated Mar. 31, 2010.

International Search Report, International Application Serial No. PCT/SE2008/000746, 7 pages, dated Apr. 7, 2009.

Knutsson, H., and Andersson, M., Morphons: Segmentation using Elastic Canvas and Paint on Priors, IEEE International Conference on Image Processing (ICIP 2005), Genova, Italy, 4 pages (2005).

Sadik, M. et al., A new computer-based decision-support system for the interpretation of bone scans, Nuclear Medicine Communications, 27(5):417-423 (2006).

Sajn, L. et al., Computerized segmentation of whole-body bone scintigrams and its use in automated diagnostics, Computer Methods and Programs in Biomedicine, 80:47-55 (2005).

Sluimer, I. et al., Toward Automated Segmentation of the Pathological Lung in CT, IEEE Transactions on Medical Imaging, 24(8):1025-1038 (2005).

Supplementary European Search Report , European Application Serial No. 08869112.6, 5 pages, dated Jun. 28, 2013.

Wrangsjo, A. et al., Non-rigid Registration Using Morphons, Proceedings of the 14th Scandinavian Conference on Image Analysis (SCIA '05), pp. 501-510 (2005).

Written Opinion, International Application Serial No. PCT/SE2008/000746, 14 pages, dated Apr. 7, 2009.

Yin, T.-K., A Computer-Aided Diagnosis for Locating Abnormalities in Bone Scintigraphy by a Fuzzy System With a Three-Step Minimization Approach, IEEE Transactions on Medical Imaging, 23(5):639-654 (2004).

Anand, A. et al., Analytic Validation of the Automated Bone Scan Index as an Imaging Biomarker to Standardize Quantitative Changes in Bone Scans of Patients with Metastatic Prostate Cancer, J. Nucl. Med., 57(1):41-45 (2016).

Anand, A. et al., Automated Bone Scan Index as a quantitative imaging biomarker in metastatic castration-resistant prostate cancer patients being treated with enzalutamide, EJNMMI Research, 6:23, 7 pages (2016).

Anand, A. et al., Translating Prostate Cancer Working Group 2 (PCWG2) Progression Criteria into a Quantitative Response Biomarker in Metastatic Castration Resistant Prostate Cancer (mCRPC), ASCO GU Conference, Poster, presented Feb. 16, 2017.

Anand, A. et al., Translating Prostate Cancer Working Group 2 (PCWG2) progression criteria into a quantitative response biomarker in metastatic castration-resistant prostate cancer (mCRPC), Journal of Clinical Oncology, 35(6):170 (2017).

Armstrong, A. et al., Assessment of the bone scan index in a randomized placebo-controlled trial of tasquinimod in men with metastatic castration-resistant prostate cancer (mCRPC), Urologic Oncology: Seminars and Original Investigations, 32:1308-1316 (2014).

Armstrong, A. et al., Development and validation of a prognostic model for overall survival in chemotherapy-naive men with metastatic castration-resistant prostate cancer (mCRPC) from the phase 3 prevail clinical trial, Journal of Clinical Oncology, 35(Suppl. 6):Abstract 138 (2017).

Armstrong, A. J. et al., Phase 3 prognostic analysis of the automated bone scan index (aBSI) in men with bone-metastatic castration-resistant prostate cancer (CRPC), Meeting Library ASC University, 1 page abstract, (2017).

Belal, S. et al., Association of PET Index quantifying skeletal uptake in NaF PET/CT images with overall survival in prostate cancer patients, ASCO GU 2017, Poster 178, presented Feb. 16, 2017.

Belal, S. et al., PET Index quantifying skeletal uptake in NaF PET/CT images with overall survival in prostate cancer patients, ASCO GU 2017, Abstract (Feb. 13, 2017).

Belal, S. L. et al, 3D skeletal uptake of $^{18}$F sodium fluoride in PET/CT images is associate with overall survival in patients with prostate cancer, EJNMMI Research, 7(15):1-8 (2017).

Belal, S.L. et al., Automated evaluation of normal uptake in different skeletal parts in 18F-sodium fluoride (NaF) PET/CT using a new convolutional neural network method, EJNMMI, EANM '17, 44(Suppl 2):5119-5956, Abstract EP-0116 (2017).

Bushberg, J. T. et al., Essential Physics of Medical Imaging, Essential Physics of Medical Imaging, 19.3: p. 581 (table 15-3), p. 713 paragraph 6, section 19.3 and p. 720, (2011).

Dennis, E. et al., Bone Scan Index: A Quantitative Treatment Response Biomarker for Castration-Resistant Metastatic Prostate Cancer, Journal of Clinical Oncology, 30(5):519-524 (2012).

GE Healthcare, SPECT/CT Cameras, retrieved Oct. 25, 2017: <http://www3.gehealthcare.com.sg/en-gb/products/categories/nuclear_medicine/spect-ct_cameras>.

Giesel, F. L. et al., F-18 labelled PSMA-1007: biodistribution, radiation dosimetry and histopathological validation of tumor lesions in prostate cancer patients, Eur. J. Nucl. Med. Mol. Imaging, 44:678-688 (2017).

Goffin, K. E. et al., Phase 2 study of $^{99m}$Tc-trofolastat SPECT/CT to identify and localize prostate cancer in intermediate- and high-risk patients undergoing radical prostatectomy and extended pelvic lymph node dissection, J. Nucl. Med., 27 pages (2017).

Goffin, K. E. et al., Phase 2 Study of 99mTc-trofolastat SPECT/CT to identify and localize prostate cancer in intermediate- and high-risk patients undergoing radical prostatectomy and extended pelvic lymph node dissection, Journal of Nuclear Medicine, pp. 1-22 with supplemental data included, (2017).

Hiller, S. M. et al., 99mTc-Labeled Small-Molecule Inhibitors of Prostate-Specific Membrane Antigen for Molecular Imaging of Prostate Cancer, Journal of Nuclear Medicine, 54(8):1369-1376 (2013) retrieved Oct. 25, 2017: <http://jnm.snmjournals.org/content/54/8/1369.full>.

Horikoshi, H. et al., Computer-aided diagnosis system for bone scintigrams from Japanese patients: importance of training database, Annals of Nuclear Medicine, 26(8):622-626 (2012).

International Search Report, PCT/US2017/058418 (Network for Medical Image Analysis, Decision Support System, and Related Graphical User Interface (GUI) Applications, filed Oct. 26, 2017), issued by ISA/European Patent Office, 4 pages, Feb. 27, 2018.

Kaboteh R. et al., Progression of bone metastases in patients with prostate cancer—automated detection of new lesions and calculation of bone scan index, EJNMMI Research, 3:64 (2013).

Kaboteh, R. et al., Convolutional neural network based quantification of choline uptake in PET/CT studies is associated with overall survival in patients with prostate cancer, EJNMMI, EANM '17, 44(Suppl 2):S119-S956, Abstract EP-0642 (2017).

(56) References Cited

OTHER PUBLICATIONS

Keiss, et al., Prostate-specific membrane antigen and a target for cancer imaging and therapy, The Quarterly Journal of Nuclear Medicine and Molecular Imaging, 59(3):241-268 (2015).
Kikuchi, A. et al., Automated segmentation of the skeleton in whole-body bone scans: influence of difference in atlas, Nuclear Medicine Communications, 33(9):947-953 (2012).
Kinahan, P.E. et al., PET/CT Standardized Update Values (SUVs) in Clinical Practice and Assessing Response to Therapy, Semin Ultrasound CT MR 31(6):496-505 (2010) retrieved Oct. 25, 2017: <https://www.ncbi.nlm.nih.gov/pmc/articles/PMC3026294/>.
Kopka, K. et al., Glu-Ureido-Based Inhibitors of Prostate-Specific Membrane Antigen: Lessons Learned During the Development of a Novel Class of Low-Molecular-Weight Theranostic Radiotracers, The Journal of Nuclear Medicine, 58(9)(Suppl. 2):17S-26S, (2017).
Liu, L. et al., Computer-Aided Detection of Prostate Cancer with MRI: Technology and Applications, Acad Radiol. Author manuscript, 50 pages 2016.
Ma, L. et al., Automatic segmentation of the prostate on CT images using deep learning and multi-atlas fusion, Proc. of SPIE vol. 10133:101332O-1-101332O-9 (2017).
Ma, L. et al., Combining Population and Patient-Specific Characteristics for Prostate Segmentation on 3D CT Images, Proc of SPIE 9784:978427-1-8 (2016).
Ma, L. et al., Random Walk Based Segmentation for the Prostate on 3D Transrectal Ultrasound Images, Proc SPIE Int Soc Opt Eng. Author manuscript, 13 pages (2016).
Mayo Clinic Staff, Choline C-11 PET scan, Overview, Mayo Clinic, 4 pages (2017), retrieved Oct. 25, 2017: <https://www.mayoclinic.org/tests-procedures/choline-c-11-pet-scan/home/ovc-20156994>.
Nakajima, K. et al., Enhanced diagnostic accuracy for quantitative bone scan using an artificial neural network system: a Japanese multi-center database project, EJNMMI Research, 3:83 (2013).
National Cancer Institute, NCI Drug Dictionary: gallium Ga 68-labeled PSMA-11, retrieved Oct. 25, 2017: <https://www.cancer.gov/publications/dictionaries/cancer-drug?cdrid=766400>.
National Cancer Institute, NCI Drug Dictionary: technetium Tc 99m methylene diphosphonate, retrieved Oct. 25, 2017: <https://www.cancer.gov/publications/dictionaries/cancer-drug?cdrid=537722>.
Perera, M. et al., Sensitivity, Specificity, and Predictors of Positive 68Ga-Prostate-specific Membrane Antigen Positron Emission Tomography in Advanced Prostate Cancer: A Systematic Review and Meta-analysis, European Urology, 70(6):926-937 (2016).
Polymeri, E. et al., Analytical validation of an automated method for segmentation of the prostate gland in CT images, EJNMMI, EANM '17, 44(Suppl 2):S119-S956, Abstract EP-0641 (2017).
radiologyinfo.org for Patients, Computed Tomography (CT), retrieved Oct. 25, 2017: <https://www.radiologyinfo.org/en/submenu.cfm?pg=ctscan>.
Rowe, S. P. et al., PET Imaging of prostate-specific membrane antigen in prostate cancer: current state of the art and future challenges, Prostate Cancer and Prostatic Diseases, 1-8 (2016).
Sabbatini, P. et al., Prognostic Significance of Extent of Disease in Bone in Patients With Androgen-Independent Prostate Cancer, Journal of Clinical Oncology, 17(3):948-957 (1999).
Sadik, M. et al., 3D prostate gland uptake of 18F-choline—association with overall survival in patients with hormone-naïve prostate cancer, The Journal of Nuclear Medicine, 58(Suppl. 1):Abstract 544 (2017).
Sadik, M. et al., Automated 3D segmentation of the prostate gland in CT images—a first step towards objective measurements of prostate uptake in PET and SPECT images, Journal of Nuclear Medicine, 58(1) (2017).
Sadik, M. et al., Automated quantification of reference levels in liver and mediastinum (blood pool) for the Deauville therapy response classification using FDG-PET/CT in lymphoma patients, EJNMMI, EANM '17, 44(Suppl 2):S119-S956, Abstract EP-0770 (2017).
Sadik, M. et al., Computer-assisted interpretation of planar whole-body bone scans, Journal Nuclear Medicine, 49(12):1958-65, 2008.
Sadik, M. et al., Convolutional neural networks for segmentation of 49 selected bones in CT images show high reproducibility, EJNMMI, EANM '17, 44(Suppl 2):S119-S956, Abstract OP-657 (2017).
Sadik, M. et al., Improved classifications of planar whole-body bone scans using a computer-assisted diagnosis system: a multicenter, multiple-reader, multiple-case study, Journal of Nuclear Medicine, 50(3): 368-75, 2009.
Sadik, M. et al., Variability in reference levels for Deauville classifications applied to lymphoma patients examined with 18F-FDG-PET/CT, EJNMMI, EANM '17, 44(Suppl 2):S119-S956, Abstract EP-0771 (2017).
Salerno, J. et al., Multiparametric magnetic resonance imaging for pre-treatment local staging of prostate cancer: A Cancer Care Ontario clinical practice guideline, Canadian Urological Association Journal, 10(9-10):332-339 (2016).
Sjöstrand K. et al., Statistical regularization of deformation fields for atlas-based segmentation of bone scintigraphy images, MICCAI 5761:664-671 (2009).
Tian, Z. et al., A fully automatic multi-atlas based segmentation method for prostate MR images, Proc SPIE Int Soc Opt Eng. Author manuscript, 12 pages (2015).
Tian, Z. et al., A supervoxel-based segmentation method for prostate MR images, Med. Phys., 44(2):558-569 (2017).
Tian, Z. et al., Deep convolutional neural network for prostate MR segmentation, Proc. of SPIE 10135:101351L-1-101351L-6 (2017).
Tian, Z., et al., Superpixel-based Segmentation for 3D Prostate MR Images, IEEE Trans Med Imaging, Author manuscript, 32 pages, (2016).
Ulmert, D. et al., A Novel Automated Platform for Quantifying the Extent of Skeletal Tumour Involvement in Prostate Cancer Patients Using the Bone Scan Index, European Urology, 62(1):78-84 (2012).
Written Opinion, PCT/US2017/058418 (Network for Medical Image Analysis, Decision Support System, and Related Graphical User Interface (GUI) Applications, filed Oct. 26, 2017), issued by ISA/European Patent Office, 9 pages, dated Feb. 27, 2018.

* cited by examiner

SYSTEM FOR DETECTING BONE CANCER METASTASES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

[This]*The present* application *is a broadening reissue application of U.S. application Ser. No. 13/639,747, filed Jan. 2, 2013, now U.S. Pat. No. 8,855,387, issued Oct. 7, 2014, which* is a nationalization under 35 U.S.C. §371 from International Application Serial No. PCT/SE2008/000746, filed Dec. 23, 2008 and published as WO 2009/084995 A1 on Jul. 9, 2009, which claims the priority benefit of U.S. Provisional Application Ser. No. 61/017,192, filed Dec. 28, 2007, the contents of which [applications and publication] are incorporated herein by reference in their entirety.

TECHNICAL FIELD

The present invention relates to the field of medical imaging and to the field of automated processing and interpretation of medical images. In particular, it relates to automated processing and interpretation of two-dimensional bone scan images produced via isotope imaging.

BACKGROUND

Interpreting medical images originating from different types of medical scans is a difficult, error prone, and time consuming work which often involves several manual steps. This is especially true when trying to determining contours of a human skeleton and cancer metastases in a medical scan image.

Therefore, there is a great need for a method for determining contours of a human skeleton and any cancer metastases, and being capable of extracting features for an automatic interpretation system.

SUMMARY OF THE INVENTION

With the above and following description in mind, then, an aspect of the present invention is to provide a method for determining contours of a human skeleton and being capable of extracting features for an automatic interpretation system, which seeks to mitigate or eliminate one or more of the above-identified deficiencies in the art and disadvantages singly or in any combination.

The object of the present invention is to provide a system and a method for fully automatic interpretation of bone scan images.

It is a further object to provide a method for reducing the need for manual work and to create an atlas image fully comparable with a normal reference image of the human skeleton. It is also an object of the present invention to provide a method for creating such a normal image.

An aspect of the present invention relates to a detection system for automatic detection of bone cancer metastases from a set of isotope bone scan images of a patients skeleton, the system comprising a shape identifier unit for identifying anatomical structures of the skeleton pictured in the set of bone scan images, forming an annotated set of images, a hotspot detection unit for detecting areas of high intensity in the annotated set of images based on information from the shape identifier regarding the anatomical structures corresponding to different portions of the skeleton of the images, a hotspot feature extraction unit for extracting a set of hotspot features for each hot spot detected by the hotspot detection unit ,a first artificial neural network unit arranged to calculate a likelihood for each hot spot of the hotspot set being a metastasis based on the set of hotspot features extracted by the hotspot feature extraction unit, a patient feature extraction unit arranged to extract a set of patient features based on the hotspots detected by the hotspot detection unit and on the likelihood outputs from the first artificial neural network unit, and a second artificial neural network unit arranged to calculate a likelihood that the patient has one or more cancer metastases, based on the set of patient features extracted by the patient feature extraction unit.

The detection system may also comprise a shape identifier unit comprising a predefined skeleton model of a skeleton, the skeleton model comprising one or more anatomical regions, each region representing an anatomical portion of a general skeleton.

The detection system may also comprise a predefined skeleton model adjusted to match the skeleton of the set of bone scan images of the patient, forming a working skeleton model.

The detection system may also comprise a hotspot detection unit comprising a threshold scanner unit for scanning the set of bone scan images and identifying pixels above a certain threshold level.

The detection system may also comprise a hotspot detection unit comprising different threshold levels for the different anatomical regions that are defined by the shape identifier unit.

The detection system may also comprise a hotspot feature extraction unit for extracting one or more hotspot features for each hot spot, comprises means for determining the shape and position of each hotspot.

The detection system may also comprise a first artificial neural network unit arranged to be fed with the features of each hotspot of the hotspot set produced by the hotspot feature extraction unit.

The detection system may also comprise a patient feature extraction unit provided with means to perform calculations that make use of both data from the hotspot feature extraction unit and of the outputs of the first artificial neural network unit.

The detection system may also comprise a second artificial neural network unit arranged to calculate the likelihood for the patient having one or more cancer metastases, and wherein the unit is fed with the features produced by the patient feature extraction unit.

A second aspect of the present invention relates to a method for automatically detecting bone cancer metastases from an isotope bone scan image set of a patient, the method comprising the following steps of extracting knowledge information from bone scan image set, processing extracted information to detect bone cancer metastases, wherein the processing involves the use of artificial neural networks.

The step of processing extracted information to detect bone cancer metastases may further involve feeding, to a pretrained artificial neural network, at least one of the following, a value describing the skeletal volume occupied by an extracted hotspot region, a value describing the maximum intensity calculated from all hotspots on the corresponding normalized image, a value describing the eccentricity of each hotspot, value describing the hotspot localization relative to a corresponding skeletal region, a value describing distance asymmetry which is only calculated for skeletal regions with a natural corresponding contralateral skeletal region, and a number of hotspots in one or more certain anatomical region(s).

The step of extracting information may further involve the steps of, identifying a number of anatomical structures in the bone scan image(s), detecting hotspots in each anatomical region by comparing the value of each pixel with a threshold value, different for each anatomical region, and decide, for each hotspot, which anatomical region it belongs to.

The method may further comprise the step of, for each hotspot, determining the number of pixels having an intensity above a predetermined threshold level.

The step of identifying a number of anatomical structures in the bone scan image(s) may further include the step of segmenting the bone scan image(s) by a segmentation-by-registration method.

The segmentation-by-registration method may further comprise the steps of, comparing a bone scan image set with an atlas image set, the atlas image having anatomical regions marked, adjusting a copy of the atlas image set to the bone scan image set, such that anatomical regions of the atlas image can be superimposed on the bone scan image.

A third aspect of the present invention relates to a method for creating a skeleton shape model, the method comprising the steps of providing images of a number of healthy reference skeletons, reorienting said images into a common coordinate system, using at least two landmark points corresponding to anatomical landmarks of the skeleton, making a statistical analysis of said images, and based on the statistical analysis, segmenting a skeleton shape model.

A fourth aspect of the present invention relates to a method for automatic interpretation of a two dimensional medicine image set representing a body organ where said method comprises the steps of automatically rotating the image set to adjust for accidental tilting when the images was originally taken, automatically finding the contours of the organ, automatically adjusting size, position, rotation, and shape of a predefined model shape of the type of organ in question to fit the organ of the current image, automatically, with the aid of the model shape, defining certain portions of the image, normalizing, the intensity of the image, quantifying each pixel in the image of the organ, producing a quantification result, feeding the quantification results to an interpretation system, letting the interpretation system interpret the image, producing an interpretation result, and presenting the interpretation result to a user.

The method according to the fourth aspect where the organ is the skeleton and said normalization is performed by assigning, to a certain area of the skeleton, a certain reference value.

A fifth aspect of the present invention relates to an image classification system for labeling an image into one of two or more classes where one class is normal and one class is pathological, the system comprising a pretrained artificial neural network having a plurality of inputs nodes, and a number of output nodes, a feature extractor, capable of extracting a number of features from said image, said features being suitable for feeding to the input nodes, wherein the pretrained artificial network presents a classification result on the number of output nodes when the number of features of the image is fed to the plurality of input nodes.

The classification system according to the fifth aspect wherein the image is a two dimensional skeleton image.

The classification system according to the fifth aspect wherein said number of features comprises a total number of pixels inside a contour of a skeleton of said skeleton image.

The classification system according to the fifth aspect wherein said number of features comprises number of pixels in largest cluster of pixels above a certain threshold level inside a contour of a skeleton of said skeleton image.

A sixth aspect of the present invention relates to a method for automatic normalization of bone scan images comprises the steps of, identifying image elements corresponding to the skeleton, identifying hotspot elements contained in the image, subtracting the hotspot elements from the skeleton elements, creating an image having remaining elements, calculating an average intensity of the remaining elements, calculating a suitable normalization factor, adjusting the bone scan image intensities by multiplication with the normalization factor.

The method according to the sixth aspect may also comprise the repetition of the steps of identifying hotspot elements contained in the image, subtracting the hotspot elements from the skeleton elements, creating an image having remaining elements, calculating an average intensity of the remaining elements, calculating a suitable normalization factor, adjusting the bone scan image intensities by multiplication with the normalization factor, which are repeated until no further significant change in the normalization factor occurs.

Any of the first, second, third, fourth, fifth, or sixth aspects presented above of the present invention may be combined in any way possible.

BRIEF DESCRIPTION OF THE DRAWINGS

Further objects, features, and advantages of the present invention will appear from the following detailed description of some embodiments of the invention, wherein some embodiments of the invention will be described in more detail with reference to the accompanying drawings, in which.

DETAILED DESCRIPTION

Embodiments of the present invention relate, in general, to the field of medical imaging and to the field of automated processing and interpretation of medical images. A preferred embodiment relates to a method for automatically or semi-automatically determining contours of a human skeleton and any cancer metastases contained therein and being capable of extracting features to be used by an automatic interpretation system An image is a digital representation wherein each pixel represents a radiation intensity, a so called "count", as known in the art, coming from a radio active substance injected into the human body prior to taking of the image.

Embodiments of the present invention will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference signs refer to like elements throughout.

Figure 1:
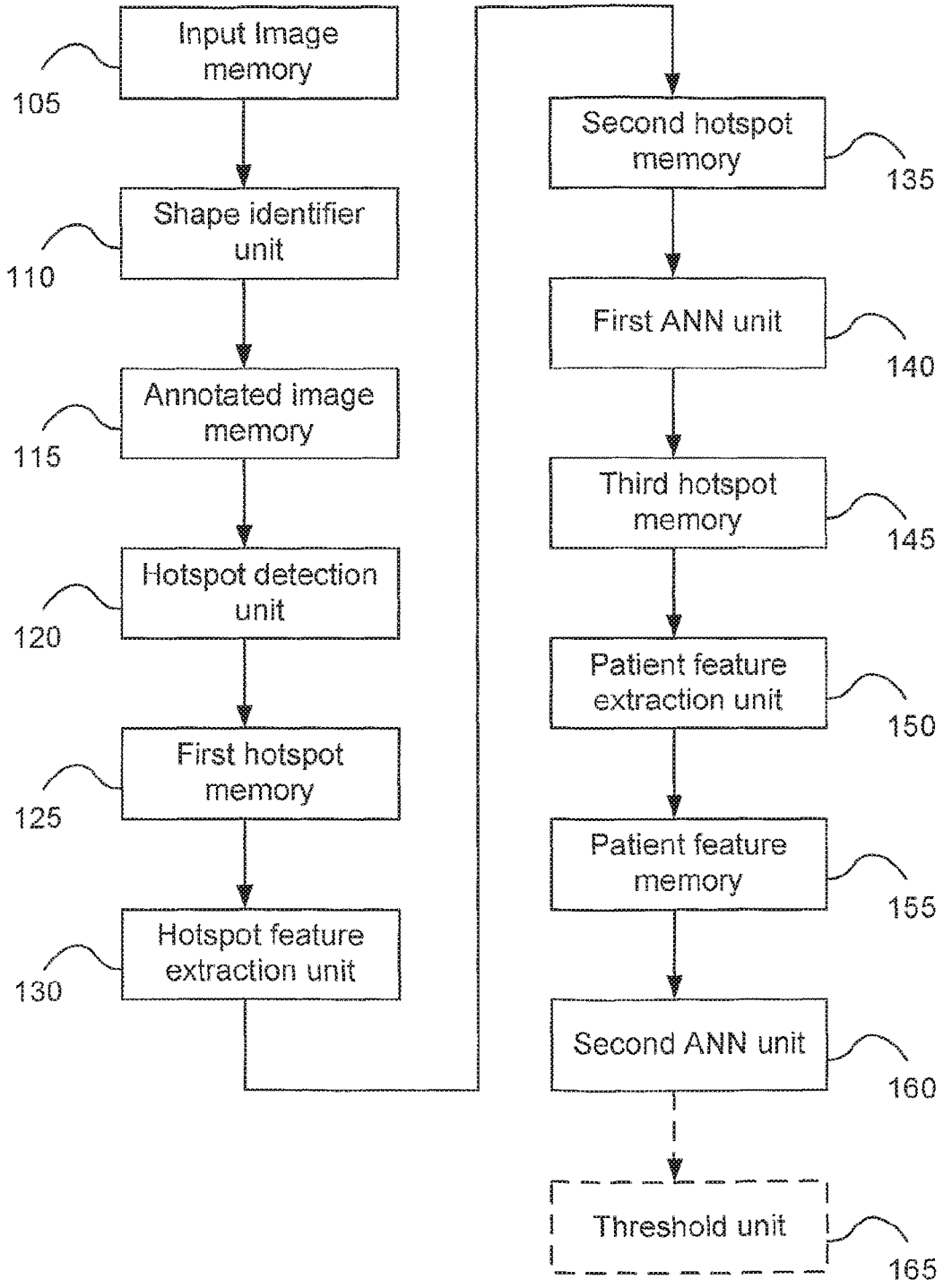
FIG. 1 shows a block diagram of a detection system for automatic detection of bone cancer metastases from a set of isotope bone scan images of a patient's skeleton.

FIG. 1 shows a block diagram of a detection system for automatic detection of bone cancer metastases from one or more sets of digital isotope bone scan images of a patient's skeleton according to an embodiment of the present invention. A set is consisting of two images: an anterior scan and a posterior scan. The system comprises an input image memory 105 for receiving and storing the sets of digital isotope bone scan images. The input image memory 105 is connected to a shape identifier unit 110 arranged to identify anatomical structures of the skeleton pictured in the set of bone scan images stored in the memory 105, forming an annotated set of images as shown in FIG. 6 where label 601 points to an outline defining one such identified anatomical structure (right femur bone). The shape identifier unit 110 of the detection system comprises a predefined model of a skeleton, the skeleton model comprising one or more anatomical regions, each region representing an anatomical portion of a general skeleton. The predefined skeleton model is adjusted to match the skeleton of the set of bone scan images of the patient, forming a working skeleton model. The shape identifier unit 110 is connected to an annotated image memory 115 to store the annotated set of images.

A hotspot detection unit 120 is connected to the annotated image memory 115 and is arranged to detect areas of high intensity in the annotated set of images stored in the memory 115 based on information from the shape identifier 110 regarding the anatomical structures corresponding to different portions of the skeleton of the set of images. In an embodiment the hotspot detection unit 120 may comprise a threshold scanner unit for scanning the set of bone scan images and identifying pixels above a certain threshold. The hotspot detection unit 120 preferably comprises different thresholds for the different anatomical regions that are defined by the shape identifier unit 110. The hotspot feature extraction unit 130 for extracting one or more hotspot features for each hot spot comprises means for determining the shape and position of each hotspot.

In another embodiment the hotspot detection unit 120 may comprises an image normalization and filtering/threshold unit for scanning the set of bone scan images and identifying pixels above a certain threshold. The hotspot feature extractions unit 130 for extracting one or more hotspot features for each hot spot comprises means for determining the shape, texture and geometry of each hotspot. A detailed enumeration and description of each extracted feature of a preferred set of extracted features is found in Annex 1.

Information thus created regarding the detected areas of high intensity, so called "hotspots", is stored in a first hotspot memory 125. A hotspot feature extraction unit 130 is connected to the first hotspot memory 125 and arranged to extract a set of hotspot features for each hot spot detected by the hotspot detection unit 120. Extracted hotspot features are stored in a second hotspot memory 135.

A first artificial neural network (ANN) unit 140 is connected to the second hotspot memory and arranged to calculate a likelihood for each hotspot of the hotspot set being a metastasis. The first artificial neural network unit 140 are fed with the features of each hotspot of the hotspot set produced by the hotspot feature extraction unit 130. The likelihood calculation is based on the set of hotspot features extracted by the hotspot feature extraction unit 130. The results of the likelihood calculations are stored in a third hotspot memory 145.

Preferably, in the first artificial neural network unit 140 there is arranged a pretrained ANN for each anatomical region. Each hotspot in a region is processed, the one after another, by the ANN arranged to handle hotspots from that region.

A patient feature extraction unit 150 is connected to the second and third hotspot memory 135, 145, and arranged to extract a set of patient features based on the number of hotspots detected by the hotspot detection unit 120 and stored in the first hotspot memory 125, and on the likelihood output values from the first artificial neural network unit 140 being stored in the third hotspot memory 145. The patient feature extraction unit 150 are provided with means to perform calculations that make use of both data from the hotspot feature extraction unit 130 and of the outputs of the first artificial neural network unit 140. The extracted patient features are stored in a patient feature memory 155. Preferably, the extracted patient features are those listed in a second portion of Annex 1.

A second artificial neural network unit 160 is connected to the patient feature memory 155, and is arranged to calculate a metastasis likelihood that the patient has one or more cancer metastases, based on the set of patient creatures extracted by the patient feature extraction unit 150 being stored in the patient feature memory 155. The system may optionally (hence the jagged line in FIG. 1) be provided with a threshold unit 165 which is arranged to, in one embodiment, make a "yes or no" decision by outputting a value corresponding to a "yes, the patient has one or more metastases" if the likelihood outputted from the second artificial neural network unit 160 is above a predefined threshold value, and by outputting a value corresponding to a "no, the patient has no metastases" if the likelihood outputted from the second artificial neural network unit 160 is below a predefined threshold value. In another optional embodiment the threshold unit 165 is arranged to stratify the output into one of four diagnoses, definitely normal, probably normal, probably metastases and definitely metastases.

Test performed with the different embodiments showed that the system according to any of the embodiments presented above performed very well. In one of the embodiments described above the sensitivity was measured to 90% and the specificity also to 90%. The test method used in this embodiment was identical to the test method described in the article A new computer-based decision-support system for the interpretation of bone scans by Sadik M. et al published in Nuclear Medicine Communication nr. 27: p. 417-423 (hereinafter referred to as Sadik et al).

In the optional embodiment described above the performance was measured at the three configurations corresponding to the thresholds used to stratify the output value into one of four diagnoses. The sensitivity and the specificity at these configurations were:

Definitely normal/probably normal: sensitivity 95.1% specificity 70.0%.

Probably normal/probably metastases: 90.2%, 87.3%.

Probably metastases/definitely metastases: 88.0%, 90.1%.

Figure 2:
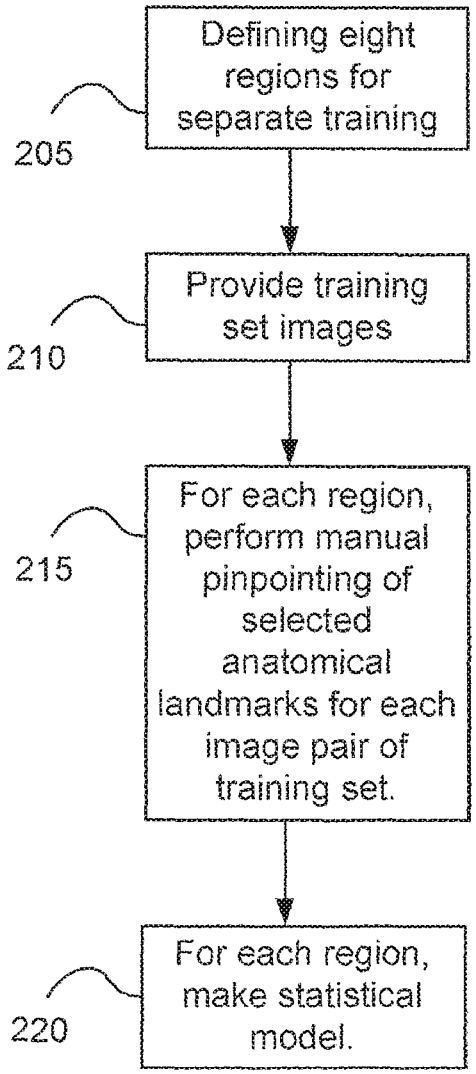
FIG. 2 shows a flowchart of a preparation method for extracting and transferring knowledge information to a computerized image processing system according to an embodiment of the present invention.

Further is provided a method for the interpretation of isotope bone scan images with the aid of the system described in conjunction with FIG. 1, prepared according to the method of FIG. 2. A method for bone scan image segmentation is provided. An embodiment of the method comprises the following steps described below and illustrated by the flowchart in FIG. 2.

The method, in an embodiment of the present invention, involves performing a delineation of the entire anterior and posterior view of the skeleton except for the lower parts of the arms and legs using an Active Shape Model (ASM) approach. Omitting said portions of the skeleton is not an issue since these locations are very rare locations for metastases and they are sometimes not acquired in the bone scanning routine. For the purpose of explaining the present invention, an Active Shape Model is defined as a statistical method for finding objects in images, said method being based on a statistical model built upon a set of training images. In each training image a shape of the object is defined by landmark points that are manually determined by a human operator during a preparation or training phase. Subsequently a point distribution model is calculated which is used to describe a general shape relating to said objects together with its variation. The general shape can then be used to search other images for new examples of the object type, e.g. a skeleton, as is the case with the present invention. A method for training of an Active Shape Model describing the anatomy of a human skeleton is provided. The model comprises the following steps described below.

A first step may be to divide a skeleton segmentation into eight separate training sets 205. The training sets are chosen to correspond to anatomical regions that the inventors have found to be particularly suitable for achieving consistent segmentation. The eight separate training sets in 210 are as follows:

1) A first training set referring to the anterior image of head and spine.
2) A second training set referring to the anterior image of the ribs.
3) A third training set referring to the anterior image of the arms.
4) A fourth training set referring to the anterior image of the lower body
5) A fifth training set referring to the posterior image of the head and spine.
6) A sixth training set referring to the posterior image of the ribs.
7) A seventh training set referring to the posterior image of the arms.
8) An eighth training set referring to the posterior image of the lower body Each training set 210 comprises a number of example images. Each image is prepared with a set of landmark points. Each landmark point is associated with a coordinate pair representing a particular anatomical or biological point of the image. The coordinate pair is determined by manually pinpointing the corresponding anatomical/biological point 215. In the anterior image the following easily identifiable anatomical landmarks are used.

Before capturing the statistics of the training set 220, each set of landmark points 215 were aligned to a common coordinate frame, different for each of the eight training sets 210. This was achieved by scaling, rotating and translating the training shapes so that they corresponded as closely as possible to each other as described in Active shape models—their training and application by T. F. Cootes, C. J. Taylor, D. H. Cooper and J. Graham presented in Computer Vision and Image Understanding, Vol. 61, no. 1, pp. 38-59, 1995 (hereinafter referred to as Cootes et al). By examination of the statistics 220 of the training sets a two-dimensional statistical point distribution model is derived that contains the shape variations observed in the training set. This statistical modeling of landmark (shape) variations across skeletons is performed as described in Cootes et al and in Application of the Active Shape Model in a commercial medical device for bone densitometry by H. H. Thodberg and A. Rosholm presented in the Proceedings of the 12th British Machine Vision Conference, 43-52, 2001, (hereinafter referred to as Thodberg et al).

The resulting statistical model 220 of shape variations can be applied to patient images in order to segment the skeleton. Starting with a mean shape, new shapes within a range of an allowable variation of the shape model can be generated similar to those of the training set such that the generated skeletons resemble the structures present in the patient image. The anterior body segments that may be segmented using this method may in one embodiment be; Cranium-Face-Neck, Spine, Sternum Upper, Sternum Lower, Right Arm, Left Arm, Right Ribs, Left Ribs, Right Shoulder, Left Shoulder, Pelvic, Bladder, Right Femur and Left Femur. The posterior body segments may in one embodiment be the Cranium, Neck, Upper Spine, Lower Spine, Spine, Right Arm, Left Arm, Right Ribs, Left Ribs, Right Scapula, Left Scapula, Ossa Coxae, Lower Pelvic, Bladder, Right Femur and the Left Femur.

A first step in a search process may be to find a start position for the mean shape of the anterior image. For instance the peak of the head may be chosen because in tests it has proved to be a robust starting position and it is easy to locate by examining the intensity in the upper part of the image above a specified threshold value in each horizontal row in the image.

The ensuing search for an instance of the skeleton shape model that fits the skeleton in the patient image is carried out in accordance with the algorithm described in Cootes et al and in Thodberg et al.

Figure 3:
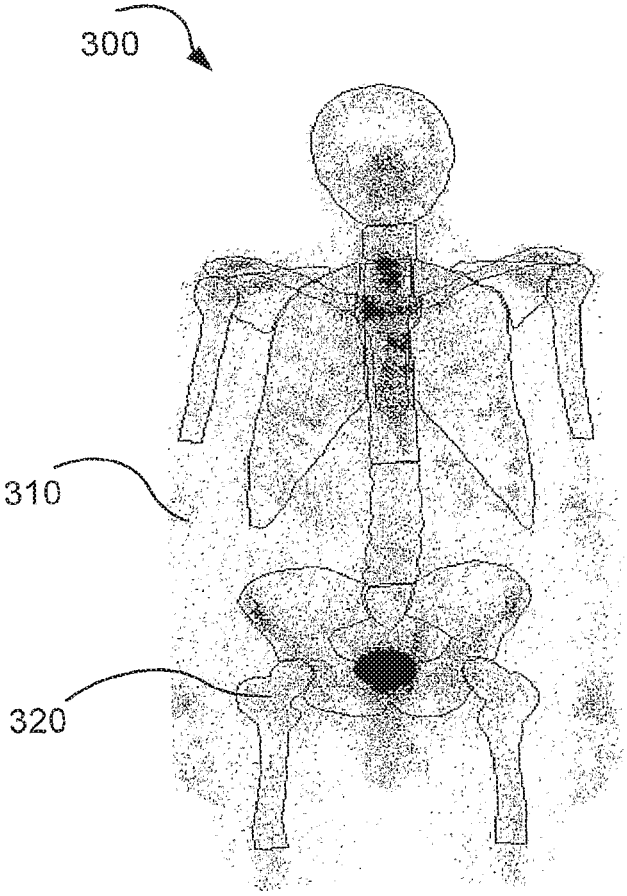
FIG. 3 shows a bone scan image wherein different anatomic regions have been identified and delineated as showed by the superimposed outlines on top of the patient image.

In another embodiment of the present invention a second method for bone scan image segmentation is provided. The goal of the second bone scan image segmentation method is as in the previous embodiment to identify and to delineate different anatomical regions of the skeleton in a bone scan image 300. These regions will be defined by superimposed outlines 320 onto the patient images 310, as shown in FIG. 3. The segmentation method described here is denoted segmentation by registration.

An image registration method transforms one image into the coordinate system of another image. It is assumed that the images depict instances of the same object class, here, a skeleton. The transformed image is denoted the source image, while the non-transformed image is denoted the target image. The coordinate systems of the source and target images are said to correspond when equal image coordinates correspond to equal geometrical/anatomical locations on the object(s) contained in the source and target images. Performing segmentation by registration amounts to using a manually defined segmentation of the source image, and registering the source image to a target image where no segmentation is defined. The source segmentation is thereby transferred to the target image, thus creating a segmentation of the target image.

Figure 4A:
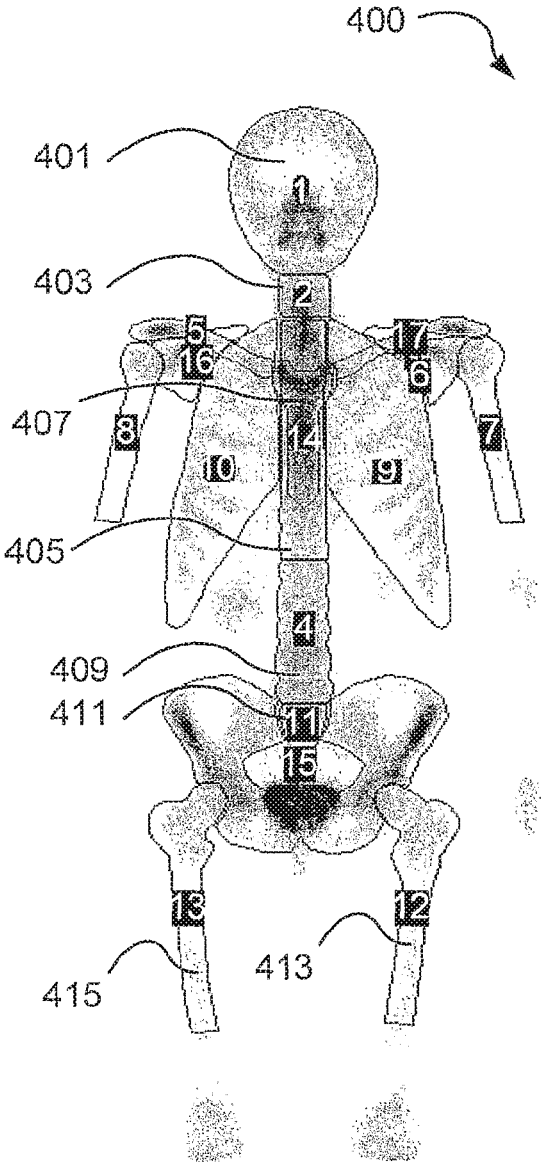
FIGS. 4a and 4b shows reference images of an average of normal healthy patient images, known as an atlas, which is intended to be transformed to resemble an unknown target patient image in order to transfer the known atlas anatomy onto the patient images.
Figure 4B:
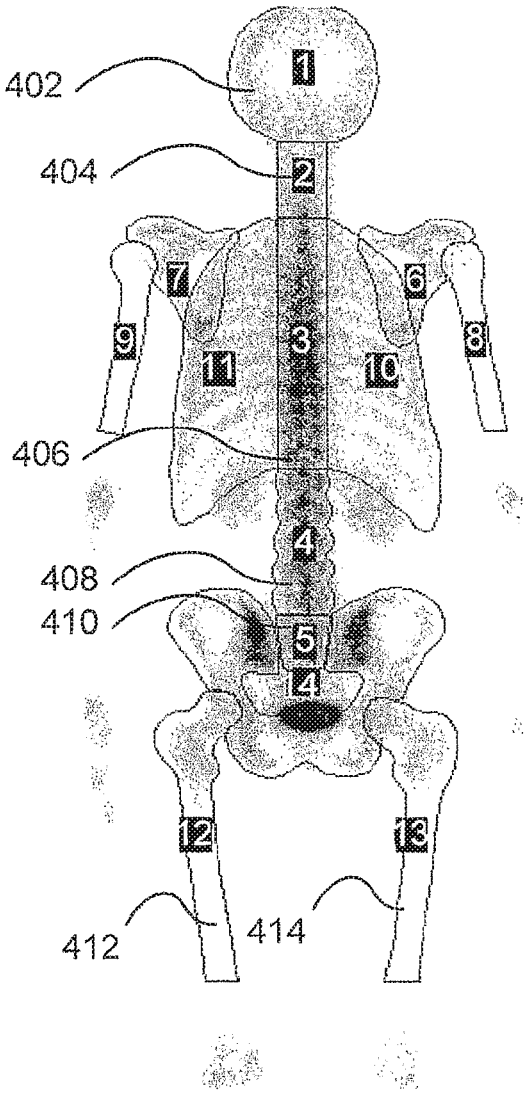

The segmentation of the source image in this embodiment defines the anatomy of a reference healthy patient and has been manually drawn by a clinical expert as a set of polygons. FIGS. 4a and 4b shows an example of such a reference healthy patient image 400, also called "atlas", wherein FIG. 4a shows the front side view or anterior side view of the patient while FIG. 4b shows backside view or the posterior view of the patient. Referring to the labels in FIGS. 4a and 4b respectively, these areas define the anterior posterior skull labeled (1,1) 401, 402, anterior and posterior cervical spine labeled (2,2) 403, 404, anterior and posterior thoracic spine labeled (3,3) 405, 406, anterior sternum labeled (14) 407, anterior and posterior lumbar spine labeled (4,4) 409, 408, anterior and posterior sacrum labeled (11,5) 411, 410, anterior and posterior pelvis labeled (15,14), anterior and posterior left and right scapula labeled (5,6,7,6), anterior left and right clavicles labeled (17,16), anterior and posterior left and right humerus labeled (7,8,9,8), anterior and posterior left and right ribs labeled (9,10,11,10), and anterior and posterior left and right femur labeled (12,13, 12,13) 413, 415, 412, 414.

The healthy reference image 400 is always used as the source image by the system, while the patient image to be examined acts as the target image. The result is a segmentation of the target image into skeletal regions as depicted in FIG. 3. Lower arms and lower legs are not considered for analysis.

The healthy reference image 400 used as the source image is constructed from 10 real examples of healthy patients with representative image quality and with normal appearance and anatomy. An algorithm is used which creates anterior and posterior images of a fictitious normal healthy patient with the average intensity and anatomy calculated from the group of example images. The system performs this task as described in Average brain models: A convergence study by Guimond A. Meunier J. Thirion J.-P presented in Computer Vision and Image Understanding, 77(2):192-210, 2000 (hereinafter referred to as Guimond et al). The result is shown in FIGS. 4a and 4b, where it can be seen that the resulting anatomy indeed has a normal healthy appearance. The anatomy exhibits a high degree of lateral symmetry which is a result of averaging the anatomy of several patients.

The registration method is an improvement of the Morphon method as described in Non-Rigid Registration using Morphons by A. Wrangsjö, J. Pettersson, H. Knutsson presented in Proceedings of the 14th Scandinavian conference on image analysis (SCIA'05), Joensuu June 2005 (hereinafter referred to as Wrangsjö et al) and in Morphons: Segmentation using Elastic Canvas and Paint on Priors by H. Knutsson, M. Andersson presented in ICIP 200, Genova, Italy. September 2005 (hereinafter referred to as Knutsson et al). The method is improved to increase robustness for the purpose of segmenting skeletal images where both an anterior image and a posterior image are supplied. We now turn to a detailed description of this improvement.

The improvement of the Morphon method contained in this invention consists of a system for using multiple images of the same object for determining a single image transformation. In particular, we use the anterior and posterior skeletal images simultaneously. The goal of the improvement is to increase robustness of the method. To describe the improvement, necessary parts of the original Morphon method are first described, followed by a description of the improvement.

The following description of the so-called displacement vector field generation used in the Morphon method serves to introduce notation and put the improvement into perspective. For a more thorough treatment, refer to Wrangsjö et al and Knutsson et al.

The Morphon registration method proceeds in iterations, where each iteration brings the source image into closer correspondence with the target image. This corresponds to a small displacement of each source image element (pixel or voxel). The collection of all such displacements during an iteration are collected in a vector field of the same size as the source image where each vector describes the displacement of the corresponding image element. The vector field is determined using 4 complex filters. Each filter captures lines and edges in the image in a certain direction. The directions corresponding to the 4 filters are vertical, horizontal, top left to bottom right diagonal and top right to bottom left diagonal. Filtering the image by one of these filters generates a complex response which can be divided into a phase and a magnitude. Due to the Fourier shift theorem, the phase difference at a particular point between the filtered source and target images is proportional to the spatial shift required to bring the objects into correspondence at that point in the direction of the filter. When the phase and magnitude at each image point has been calculated for all 4 filter directions, the displacement vector can be found by solving a least-squares problem at each point. The magnitude can be used to derive a measure of the certainty of each displacement estimate. The certainties can be incorporated in the least-squares problem as a set of weights. The resulting weighted least squares problem is $$\min_{v} \sum_{i=0}^{3} [w_i n_i^T v - v_i]^2 \tag{1}$$

where v is the sought 2-by-1 displacement vector, $n_i$ is the direction of the ith filter, $v_i$ is the phase difference corresponding to the ith filter and $w_i$ is the certainty measure derived from the magnitude of to the ith filter.

The improvement of this method contained in present invention consists of using more than one image for estimating a single vector field of displacements. Each image is filtered separately as described above, resulting in 4 complex responses for each image. The weighted least squares problem is expanded to include all images yielding $$\min_{v} \sum_{j=0}^{k-1} \sum_{i=0}^{3} [w_{i,k} n_i^T v - v_{i,k}]^2 \tag{2}$$

where k is the number of images (2 in the case of skeletal images). The effect of this is that the number of data points are multiplied by the number of images in the estimation of the two-dimensional displacement v, making the problem better defined. A further explanation of the development is provided by the certainty measures. Using a single image as input, regions of the resulting displacement vector field corresponding to low certainty measures will be poorly defined. If more than one image is supplied, chances are that at least one image is able to provide adequate certainty to all relevant regions.

As mentioned before, the hotspot detection unit 120 uses information from the shape identifier unit 110 described in conjunction with FIG. 1. It's purpose is two-fold. It's primary purpose is to segment hot pots in the anterior and posterior patient images. Hotspots are isolated image regions of high intensity and may be indicative of metastatic disease when located in the skeleton. The secondary purpose of unit 120 is to adjust the brightness of the image to a predefined reference level. Such intensity adjustment is denoted image normalization. This invention describes an algorithm which segments hot spots and estimates a normalization factor simultaneously, and is performed separately on the anterior and posterior images. First, the need for proper normalization is briefly explained, followed by a description of the algorithm.

Skeletal scintigraphy images differ significantly in intensity levels across patients, studies and hardware configurations. The difference is assumed multiplicative and zero intensity is assumed to be a common reference level for all images. Normalizing a source image with respect to a target image therefore amounts to finding a scalar factor that brings the intensities of the source image to equal levels with the target image. The intensities of two skeletal images are here defined as equal when the average intensity of healthy regions of the skeleton in the source image is equal to the corresponding regions in the target image. The normalization method, shown in a flowchart in FIG. 5, comprises the following steps.

1. Identification of image elements corresponding to the skeleton 510.
2. Identification of hotspots contained in the image 520.
3. Subtraction of hotspot elements from the skeleton elements 530.
4. Calculation of the average intensity of the remaining (healthy) elements 540.
5. Calculation of a suitable normalization factor 550.
6. Adjustment of the source image intensities by multiplication with the normalization factor 560.

The step in 510 is carried out using information on image regions belonging to the skeleton provided by the transformed anatomical regions derived by the shape identifier unit 110 of FIG. 1, as described above. The polygonal regions are converted into binary image masks which define image elements belonging to the respective regions of the skeleton.

In step 520 the hotspots are segmented using one image filtering operation and one thresholding operation. The image is filtered using a difference-of-Gaussians band-pass filter which emphasizes small regions of high intensity relative to their respective surroundings. The filtered image is then thresholded at a constant level, resulting in a binary image defining the hotspot elements.

In step 530 any of the elements calculated in 510 that coincide with the hotspot elements calculated in 520 are removed. The remaining elements are assumed to correspond to healthy skeletal regions.

In step 540 the average intensity of the healthy skeletal elements is calculated. Denote this average intensity by A.

In step 550 a suitable normalization factor is determined in relation to a predefined reference intensity level. This level may for instance be set to 1000 here. The normalization factor B is calculated as B=1000/A.

In step 560 the intensities of the source image are adjusted by multiplication by B.

The hotspot segmentation described in 520 is dependent on the overall intensity level of the image which in turn is determined by the normalization factor calculated in 550. However, the normalization factor calculated in 550 is dependent on the hotspot segmentation from 520. Since the results of 520 and 550 are interdependent, 520 to 560 may in an embodiment be repeated 570 until no further change in the normalization factor occurs. Extensive tests have shown that this process normally converges in 3 or 4 repetitions.

Figure 5:
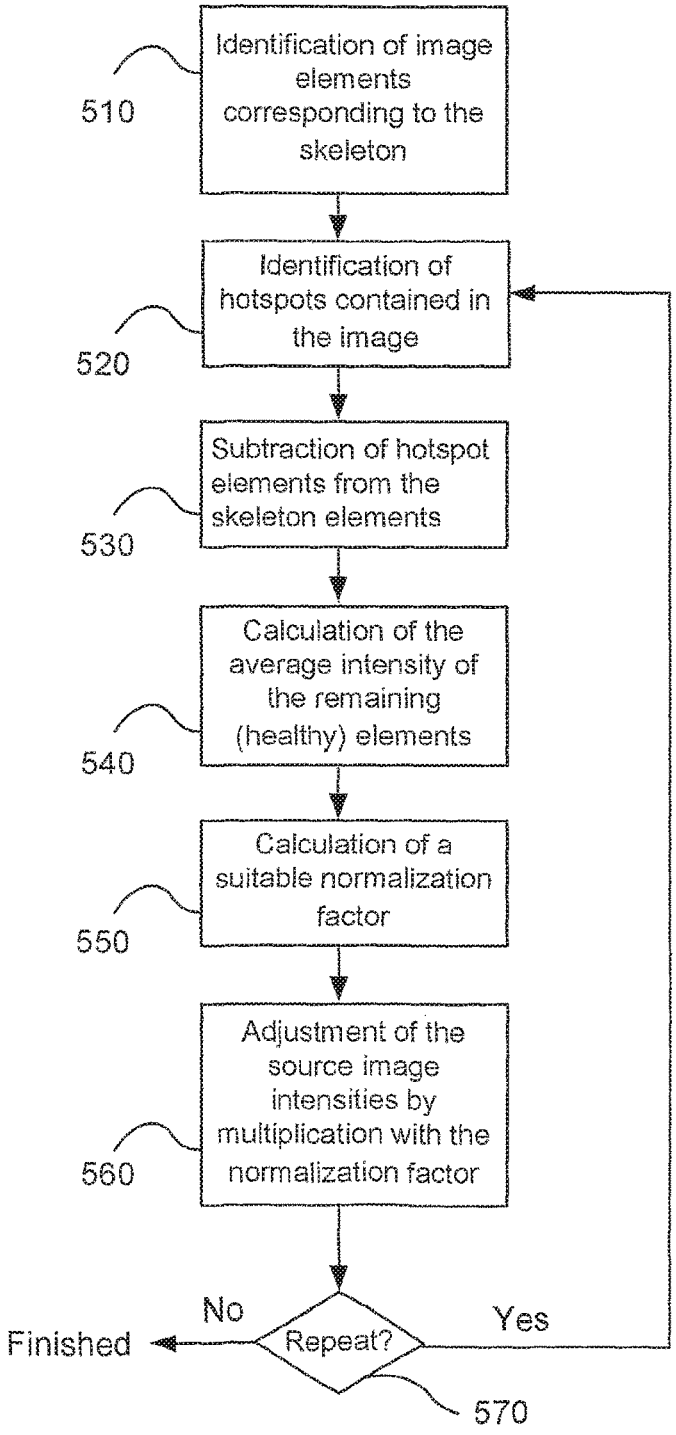
FIG. 5 shows a flowchart of a normalization method for bone scan image aimed to enhance local segmented hotspots in the image.
Figure 6A:
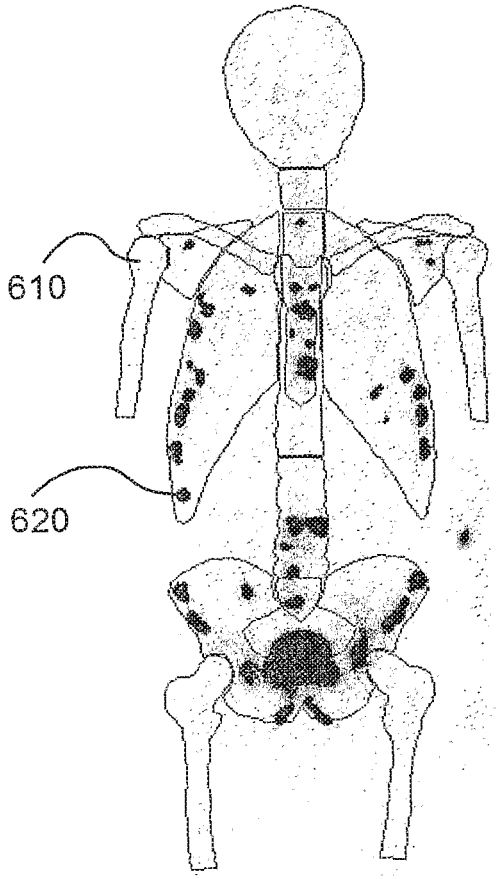
FIGS. 6a and 6b shows an example of hotspots in a patient images wherein the hotspots are regions of locally elevated intensity that may be indicative of metastatic disease.
Figure 6B:
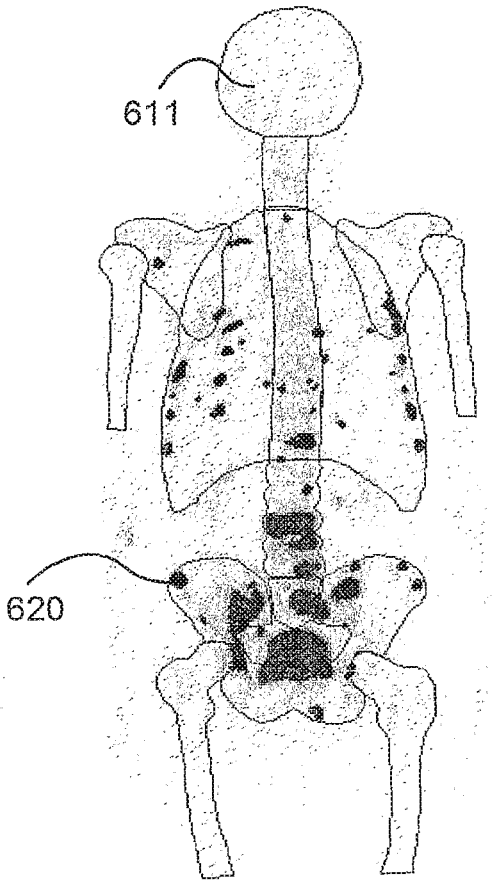

FIG. 6a shows a normalized anterior bone scan image and 6b shows a posterior normalized, bone scan image according to the normalization method in FIG. 5. The segmented hotspots 620 are shown in FIGS. 6a and 6b as dark spots appearing in the segmented image 610. Thus, an automated system according to the present invention would classify the patient as having cancer metastases.

In the above description the second ANN may in one embodiment be the same or a part of the first ANN.

In the above description the term point may be used to denote one or more pixels in an image.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein.

The foregoing has described the principles, preferred embodiments and modes of operation of the present invention. However, the invention should be regarded as illustrative rather than restrictive, and not as being limited to the particular embodiments discussed above. The different features of the various embodiments of the invention can be combined in other combinations than those explicitly described. It should therefore be appreciated that variations may be made in those embodiments by those skilled in the art without departing from the scope of the present invention as defined by the following claims.

ANNEX 1

The artificial neural network system, i.e., the first ANN unit 140, is fed with the following set of 27 features measuring the size, shape, orientation, localization and intensity distribution of each hotspot. The features are:

Skeletal involvement. Measures the skeletal volume occupied by the extracted hotspot region, based on the two-dimensional hotspot area, the two-dimensional area of the corresponding skeletal region and a coefficient representing the volumetric proportion represented by the skeletal region in relation to the entire skeleton. Calculated as (hotspot area/regional area) *coefficient.

Relative area. Hotspot area relative to the corresponding skeletal region. A measure that is independent of image resolution and scanner field-of-view.

Relative centroid position (2 features). Centroid position relative to the bounding box of the corresponding skeletal region. Values range from 0 (top, left) to 1 (bottom, right).

Relative center of mass (2 features). Similar to the centroid features, but takes the intensities of the hotspot region into account when calculating x and y values.

Relative height. Hotspot height relative to the height of the corresponding skeletal region.

Relative width. Hotspot width relative to the width of the corresponding skeletal region.

Minimum intensity. Minimum intensity calculated from all hotspot elements on the corresponding normalized image.

Maximum intensity. Maximum intensity calculated from all hotspot elements on the corresponding normalized image.

Sum of intensities. Sum of intensities calculated from all hotspot elements on the corresponding normalized image.

Mean intensity. Mean intensity calculated from all hotspot elements on the corresponding normalized image.

Standard deviation of intensities. Standard deviation of intensities calculated from all hotspot elements on the corresponding normalized image.

Boundary length. Length of the boundary of the hotspot measured in pixels.

Solidity. Proportion of the convex hull area of the hotspot represented by the hotspot area.

Eccentricity. Elongation of the hotspot ranging from 0 (a circle) to 1 (a line).

Total number of hotspot counts. Sum of intensities in all hotspots in the entire skeleton.

Regional number of hotspot counts. Sum of intensities in hotspots contained in the skeletal region corresponding to the present hotspot.

Total hotspot extent. Area of all hotspots in the entire skeleton relative to the entire skeletal area in the corresponding image.

Regional hotspot extent. Area of all hotspots in the skeletal region corresponding to the present hotspot relative to the area of the skeletal region.

Total number of hotspots. Number of hotspots in the entire skeleton.

Regional number of hotspots. Number of hotspots in the skeletal region corresponding to the present hotspot.

Hotspot localization (2 features). X-coordinate ranges from 0 (most medial) to 1 (most distal) in relation to a medial line calculated from the transformed reference anatomy in the shape identification step. Y-coordinate ranges from 0 (most superior) to 1 (most inferior). All measures are relative to the corresponding skeletal region.

Distance asymmetry. The smallest Euclidean distance between the relative center of mass of the present hotspot and the mirrored relative center of mass of hotspots in the contralateral skeletal region. Only calculated for skeletal regions with a natural corresponding contralateral skeletal region.

Extent asymmetry. The smallest difference in extent between the present hotspot and the extent of hotspots in the contralateral skeletal region.

Intensity asymmetry. The smallest difference in intensity between the present hotspot and the intensity of hotspots in the contralateral skeletal region.

The second ANN unit which determines a patient-level diagnosis pertaining to the existence of metastatic disease uses the 34 features listed below as input. All features used by the second ANN unit are calculated from hotspots classified as having high metastasis probability by file first ANN unit.

Total involvement. The summed skeletal involvement in the entire skeleton.

Skull involvement. The summed skeletal involvement in the skull region.

Cervical column involvement. The summed skeletal involvement in the cervical column region.

Thoracic column involvement. The summed skeletal involvement in the thoracic column region.

Lumbar column involvement. The summed skeletal involvement in the lumbar column region.

Upper limb involvement. The summed skeletal involvement in the upper limb region.

Lower limb involvement. The summed skeletal involvement in the lower limb region.

Thoracic involvement. The summed skeletal involvement in the thoracic region.

Pelvis involvement. The summed skeletal involvement in the pelvis region.

Total number of "high" hotspots.

Number of "high" hotspots in the skull region.

Number of "high" hotspots in the cervical column region.

Number of "high" hotspots in the thoracic column region.

Number of "high" hotspots in the lumbar column region.

Number of "high" hotspots in the upper limb region.

Number of "high" hotspots in the lower limb region.

Number of "high" hotspots in the thoracic region.

Number of "high" hotspots in the pelvis region.

Maximal ANN output from the first ANN unit in the skull region.

Maximal ANN output from the first ANN unit in the cervical spine region.

Maximal ANN output from the first ANN unit in the thoracic spine region.

Maximal ANN output from the first ANN unit in the lumbar spine region.

Maximal ANN output from the first ANN unit in the sacrum region.

Maximal ANN output from the first ANN unit in the humerus region.

Maximal ANN output from the first ANN unit in the clavicle region.

Maximal ANN output from the first ANN unit in the scapula region.

Maximal ANN output from the first ANN unit in the femur region.

Maximal ANN output from the first ANN unit in the sternum region.

Maximal ANN output from the first ANN unit in the costae region.

2nd highest ANN output from the first ANN unit in the costae region.

3rd highest ANN output from the first ANN unit in the costae region.

Maximal ANN output from the first ANN unit in the pelvis region.

2nd highest ANN output from the first ANN unit in the pelvis region.

3rd highest ANN output from the first ANN unit in the pelvis region.

The invention claimed is:

1. A detection system for automatic detection of bone cancer metastases from a set of isotope bone scan images of a patients skeleton, the system comprising:

a shape identifier unit for identifying anatomical structures of the skeleton pictured in the set of bone scan images, forming an annotated set of images;

a hotspot detection unit for detecting areas of high intensity in the annotated set of images based on information from the shape identifier regarding the anatomical structures corresponding to different portions of the skeleton of the images;

a hotspot feature extraction unit for extracting a set of hotspot features for each hot spot detected by the hotspot detection unit;

a first artificial neural network unit arranged to calculate a likelihood for each hot spot of the hotspot set being a metastasis based on the set of hotspot features extracted by the hotspot feature extraction unit;

a patient feature extraction unit arranged to extract a set of patient features based on the hotspots detected by the hotspot detection unit and on the likelihood outputs from the first artificial neural network unit; [and]

a second artificial neural network unit arranged to calculate a likelihood that the patient has one or more cancer metastases, based on the set of patient features extracted by the patient feature extraction unit*; and*

*an input image memory,*

*wherein the shape identifier unit accesses the set of isotope bone scan images from the input image memory and wherein, upon extraction of the set of patient features, the patient feature extraction unit stores the set of patient features in a patient feature memory for accessing by the second artificial neural network to calculate the likelihood that the patient has one or more cancer metastases.*

2. The detection system as recited in claim 1, wherein the shape identifier unit comprises a predefined skeleton model of a skeleton, the skeleton model comprising one or more anatomical regions, each region representing an anatomical portion of a general skeleton.

3. The detection system as recited in claim 2, wherein the predefined skeleton model is adjusted to match the skeleton of the set of bone scan images of the patient, forming a working skeleton model.

4. The detection system as recited in claim 1, wherein the hotspot detection unit comprises a threshold scanner unit for scanning the set of bone scan images and identifying pixels above a certain threshold level.

5. The detection system as recited in claim 4, wherein the hotspot detection unit comprises different threshold levels for the different anatomical regions that are defined by the shape identifier unit.

6. The detection system as recited in claim 1, wherein the hotspot feature extraction unit for extracting one or more hotspot features for each hot spot, comprises means for determining the shape and position of each hotspot.

7. The detection system as recited in claim 1, wherein the first artificial neural network unit are fed with the features of each hotspot of the hotspot set produced by the hotspot feature extraction unit.

8. The detection system as recited in claim 1, wherein the patient feature extraction unit are provided with means to perform calculations that make use of both data from the hotspot feature extraction unit and of the outputs of the first artificial neural network unit.

9. The detection system as recited in claim 1, wherein the second artificial neural network unit is arranged to calculate the likelihood for the patient having one or more cancer metastases, and wherein the unit are fed with the features produced by the patient feature extraction unit.

10. A method automatically detecting bone cancer metastases from an isotope bone scan image set of a patient, the method comprising [the following steps]:

[identifying] *accessing, by a computerized image processing system, an isotope bone scan image set, wherein each image in the isotope bone scan image set comprises a plurality of pixels with a value of each pixel corresponding to an intensity;*

*automatically segmenting, by the computerized image processing system, each image in the isotope bone scan image set to identify one or more* anatomical structures of [the] *a* skeleton pictured in the [set of] *each image in the isotope* bone scan [images] *image set, thereby* forming an annotated set of images;

*automatically* detecting [areas], *by the computerized image processing system, a set of hotspots comprising one or more hotspots, each hotspot corresponding to an area* of high intensity in the annotated set of images based on information regarding the anatomical structures corresponding to different portions of the skeleton [of the images], *said detecting of the set of hotspots comprising iteratively:*

*identifying one or more skeletal image elements, each of the skeletal image elements corresponding to a region of an image in the annotated image set, wherein the region is associated with one of the anatomical structures;*

*detecting one or more hotspots in the annotated set of images, each hotspot corresponding a region of high intensity relative to its surroundings;*

*for each of the skeletal image elements, determining whether each of the skeletal image element comprises a detected hotspot;*

*calculating an average intensity of the skeletal image elements determined not to comprise a detected hotspot;*

*calculating a normalization factor, wherein a product of the normalization factor and the average intensity is a pre-defined intensity level; and*

*multiplying the value of each pixel in the annotated set of images by the normalization factor*;

*for each hotspot in the set of hotspots,* extracting, *by the computerized image processing system,* a set of hotspot features [for each hot spot detected] *associated with the hotspot*; *and*

[feeding, to a first artificial neural network unit arranged to calculate] *for each hotspot in the set of hotspots, calculating, by the computerized image processing system,* a *first likelihood value corresponding to a* likelihood [for each hot spot] of the hotspot [set] being a metastasis, *based on* the set of hotspot features [extracted;

extracting a set of patient features based on the hotspots detected and on the likelihood outputs from the first artificial neural network unit; and feeding, to a second artificial neural network unit arranged to calculate a likelihood that the patient has one or more cancer metastases, the set of patient features extracted] *associated with the hotspot.*

11. The method of claim 10, wherein [the step of processing extracted information further involves feeding, to the pretrained artificial neural network,] *for each hotspot in the set of hotspots, the set of hotspot features comprises* at least one *feature selected from the group consisting* of [the following]:

a value describing the eccentricity of each hotspot;

a value describing the skeletal volume occupied by an extracted hotspot region;

a value describing the maximum intensity calculated from all hotspots on the corresponding normalized image;

a value describing the hotspot localization relative to a corresponding skeletal region;

a value describing distance asymmetry which is only calculated for skeletal regions with a natural corresponding contralateral skeletal region(s); *and* a number of hotspots in one or more certain anatomical region(s).

12. The method of claim 10, wherein [the step of extracting information involves the further steps of:

identifying a number of anatomical structures in the bone scan image(s);] *detecting a set of hotspots comprising one or more hotspots comprises:* detecting hotspots in each anatomical region by comparing the value of each pixel with a threshold value, different for each anatomical region; *and*

[decide] *deciding*, for each hotspot, which anatomical region it belongs to.

13. The method of claim 12 further comprising the step of:

for each hotspot: determining the number of pixels having an intensity above a predetermined threshold level.

14. The method of claim [12 wherein the step of identifying a number of anatomical structures in the] *10, comprising segmenting each image in the isotope* bone scan [image(s) further includes the step of segmenting the bone scan image(s)] *image set* by a segmentation-by-registration method.

15. The method of claim 14 wherein the segmentation-by-registration method comprises the following steps:

comparing [a] *each image of the* bone scan image set with [an] *a corresponding* atlas image *of an atlas image* set, [the] *each* atlas image having anatomical regions marked; and

*for each image of the bone scan image set,* adjusting a copy of the *corresponding* atlas image [set] to the bone scan image [set], such that anatomical regions of the atlas image can be superimposed on the [bone scan] image *of the bone scan image set*.

16. The method of claim 10, wherein [the step of processing extracted information further involves feeding, to the pretrained artificial neural network.] *for each hotspot in the set of hotspots, the set of hotspot features comprises* at least:

a value describing distance asymmetry which is only calculated for skeletal regions with a natural corresponding contralateral skeletal region.

*17. The method of claim 10, comprising calculating, for each hotspot in the set of hotspots, the first likelihood value using a pre-trained machine learning technique.*

*18. The method of claim 17, wherein the pre-trained machine learning technique is an artificial neural network (ANN).*

*19. The method of claim 10, wherein, for each hotspot in the set of hotspots, the first likelihood value corresponds to an output of a machine learning module that implements a pre-trained machine learning technique, and the output of the machine learning module is based at least in part on one or more of the hotspot features associated with the hotspot.*

*20. The method of claim 10, wherein for each hotspot in the set of hotspots, calculating the first likelihood value corresponding to a likelihood of the hotspot being a metastasis, based on the set of hotspot features associated with the hotspot comprises:*

*determining from the one or more identified anatomical structures, an anatomical structure to which the hotspot belongs based on a location of the hotspot,*

*selecting one of a set of artificial neural networks (ANNs), wherein each ANN in the set of ANNs is associated with a specific identified anatomical structure of the one or more identified anatomical structures, and*

*calculating the first likelihood value using the selected ANN, wherein the specific identified anatomical structure with which the selected ANN is associated is the anatomical structure to which the hotspot belongs.*

*21. The method of claim 10, comprising calculating, by the computerized image processing system, a second likelihood value corresponding to an overall likelihood that the patient has one or more metastases based on the calculated first likelihood values.*

*22. The method of claim 21, comprising:*

*for each hotspot in the set of hotspots, calculating the first likelihood value using a first artificial neural network (ANN), wherein:*

*the first likelihood value corresponds to an output of the first ANN, and*

*the output of the first ANN is based at least in part one or more hotspot features in the set of hotspot features associated with the hotspot; and*

*calculating the second likelihood value based on an output of a second ANN, wherein:*

*the output of the second ANN is based at least in part on one or more patient features, and*

*each of the one or more patient features is based at least in part on one or more of the first likelihood values calculated for each hotspot in the set of hotspots.*

* * * * *